(12) United States Patent
Miller

(10) Patent No.: US 11,612,734 B2
(45) Date of Patent: Mar. 28, 2023

(54) METHOD TO SECURE AN ELASTIC COMPONENT IN A VALVE

(71) Applicant: AngioDynamics, Inc., Latham, NY (US)

(72) Inventor: Stephen Miller, Queensbury, NY (US)

(73) Assignee: AngioDynamics, Inc., Latham, NY (US)

( * ) Notice: Subject to any disclaimer, the term of this patent is extended or adjusted under 35 U.S.C. 154(b) by 128 days.

(21) Appl. No.: 17/115,347

(22) Filed: Dec. 8, 2020

(65) Prior Publication Data
US 2021/0085953 A1 Mar. 25, 2021

Related U.S. Application Data

(63) Continuation of application No. 16/229,469, filed on Dec. 21, 2018, now Pat. No. 10,874,845, which is a continuation of application No. 14/272,918, filed on May 8, 2014, now Pat. No. 10,159,830, which is a continuation of application No. 13/176,054, filed on Jul. 5, 2011, now Pat. No. 8,753,320, which is a continuation of application No. 12/501,809, filed on Jul. 13, 2009, now Pat. No. 8,007,468.

(51) Int. Cl.
*A61M 39/24* (2006.01)
*A61M 1/36* (2006.01)
*A61M 39/22* (2006.01)

(52) U.S. Cl.
CPC .......... *A61M 39/24* (2013.01); *A61M 1/3653* (2013.01); *A61M 1/3659* (2014.02); *A61M 39/22* (2013.01); *A61M 2039/242* (2013.01); *A61M 2039/2426* (2013.01); *Y10T 29/49412* (2015.01)

(58) Field of Classification Search
CPC .......... A61M 1/3653; A61M 2039/242; A61M 2039/2426; A61M 39/24; A61M 39/22
See application file for complete search history.

(56) References Cited

U.S. PATENT DOCUMENTS

| 500,745 A | 7/1893 | Rogers |
|---|---|---|
| 1,142,525 A | 6/1915 | Maag |
| 1,244,379 A | 10/1917 | William |
| 1,989,145 A | 1/1935 | Newby |
| 2,122,299 A | 6/1938 | Sloan |
| 2,446,571 A | 8/1948 | Browne |
| 2,720,881 A | 10/1955 | John |

(Continued)

FOREIGN PATENT DOCUMENTS

| CN | 102155808 | 8/2011 |
|---|---|---|
| DE | 3048203 | 7/1982 |

(Continued)

OTHER PUBLICATIONS

Asch, "Venous access: options, approaches and issues," Can. Assoc Radiol. J , vol. 52, No. 3, pp. 153-164 (2001) 12 pages.

(Continued)

*Primary Examiner* — Deanna K Hall
(74) *Attorney, Agent, or Firm* — DLA Piper LLP (US)

(57) ABSTRACT

An apparatus for controlling fluid flow to provide long-term access to the vascular system, and methods of making the same, are disclosed. Exemplary embodiments of the present invention describe a wedge or other similarly shaped geometrical features for fixing an elastic component and controlling an internal stress of the elastic component.

20 Claims, 2 Drawing Sheets

(56) References Cited

U.S. PATENT DOCUMENTS

| | | |
|---|---|---|
| 2,755,060 A | 7/1956 | Raymond |
| 2,841,166 A | 7/1958 | Auzin |
| 3,020,913 A | 2/1962 | Heyer |
| 3,111,125 A | 11/1963 | Schulte |
| 3,113,586 A | 12/1963 | Edmark, Jr. |
| 3,118,468 A | 1/1964 | Bochan |
| 3,159,175 A | 12/1964 | MacMillan |
| 3,159,176 A | 12/1964 | Russell |
| RE26,235 E | 7/1967 | Woodford |
| 3,422,844 A | 1/1969 | Grise |
| 3,477,438 A | 11/1969 | Allen |
| 3,514,438 A | 5/1970 | Bixler |
| 3,525,357 A | 8/1970 | Koreski |
| 3,621,557 A | 11/1971 | Cushman |
| 3,662,955 A | 5/1972 | Takanashi |
| 3,669,323 A | 6/1972 | Harker |
| 3,673,612 A | 7/1972 | Merrill |
| 3,674,183 A | 7/1972 | Venable |
| 3,710,942 A | 1/1973 | Rosenberg |
| 3,788,327 A | 1/1974 | Donowitz |
| 3,811,466 A | 5/1974 | Ohringer |
| 3,827,456 A | 8/1974 | Sheppard |
| 3,848,579 A | 11/1974 | Villa |
| 3,885,561 A | 5/1975 | Cami |
| 3,888,249 A | 6/1975 | Spencer |
| 3,941,149 A | 3/1976 | Mittleman |
| 3,955,594 A | 5/1976 | Snow |
| 3,964,509 A | 6/1976 | Daubenberger |
| 4,000,740 A | 1/1977 | Mittleman |
| 4,072,146 A | 2/1978 | Howes |
| 4,134,402 A | 1/1979 | Mahurkar |
| 4,137,152 A | 1/1979 | Chester |
| 4,142,525 A | 3/1979 | Binard |
| 4,143,853 A | 3/1979 | Abramson |
| 4,176,678 A | 12/1979 | Le |
| 4,232,677 A | 11/1980 | Leibinsohn |
| 4,244,379 A | 1/1981 | Smith |
| 4,327,722 A | 5/1982 | Groshong |
| 4,342,315 A | 8/1982 | Jackson |
| 4,387,879 A | 6/1983 | Tauschinski |
| 4,405,316 A | 9/1983 | Mittleman |
| 4,417,888 A | 11/1983 | Cosentino |
| 4,424,058 A | 1/1984 | Parsons |
| 4,424,833 A | 1/1984 | Spector |
| 4,431,426 A | 2/1984 | Groshong |
| 4,434,810 A | 3/1984 | Atkinson |
| 4,447,237 A | 5/1984 | Frisch |
| 4,465,102 A | 8/1984 | Rupp |
| 4,468,224 A | 8/1984 | Enzmann |
| 4,475,898 A | 10/1984 | Brodner |
| 4,502,502 A | 3/1985 | Krug |
| 4,524,805 A | 6/1985 | Hoffman |
| 4,529,399 A | 7/1985 | Groshong |
| 4,543,087 A | 9/1985 | Sommercorn |
| 4,549,879 A | 10/1985 | Groshong |
| 4,552,553 A | 11/1985 | Schulte |
| 4,559,046 A | 12/1985 | Groshong |
| 4,610,276 A | 9/1986 | Paradis |
| 4,610,665 A | 9/1986 | Matsumoto |
| 4,616,768 A | 10/1986 | Flier |
| 4,625,245 A | 11/1986 | White |
| 4,626,245 A | 12/1986 | Weinstein |
| 4,646,945 A | 3/1987 | Steiner |
| 4,668,221 A | 5/1987 | Luther |
| 4,671,796 A | 6/1987 | Groshong |
| 4,673,393 A | 6/1987 | Suzuki |
| 4,681,572 A | 7/1987 | Tokarz |
| 4,692,141 A | 9/1987 | Mahurkar |
| 4,692,146 A | 9/1987 | Hilger |
| 4,701,166 A | 10/1987 | Groshong |
| 4,722,725 A | 2/1988 | Sawyer |
| 4,728,006 A | 3/1988 | Drobish |
| 4,737,152 A | 4/1988 | Alchas |
| 4,753,640 A | 6/1988 | Nichols |
| 4,790,817 A | 12/1988 | Luther |
| 4,790,832 A | 12/1988 | Lopez |
| 4,798,594 A | 1/1989 | Hillstead |
| 4,801,297 A | 1/1989 | Mueller |
| 4,809,679 A | 3/1989 | Shimonaka |
| 4,813,934 A | 3/1989 | Engelson |
| 4,842,591 A | 6/1989 | Luther |
| 4,908,028 A | 3/1990 | Colon |
| 4,944,726 A | 7/1990 | Hilal |
| 4,946,448 A | 8/1990 | Richmond |
| 4,950,252 A | 8/1990 | Luther |
| 4,960,412 A | 10/1990 | Fink |
| 4,973,319 A | 11/1990 | Melsky |
| 4,986,814 A | 1/1991 | Burney |
| 4,991,745 A | 2/1991 | Brown |
| 4,994,046 A | 2/1991 | Wesson |
| 4,995,863 A | 2/1991 | Nichols |
| 4,998,919 A | 3/1991 | Schnepp-Pesch |
| 5,000,745 A | 3/1991 | Guest |
| 5,009,391 A | 4/1991 | Steigerwald |
| 5,030,210 A | 7/1991 | Alchas |
| 5,062,836 A | 11/1991 | Wendell |
| 5,084,015 A | 1/1992 | Moriuchi |
| 5,085,635 A | 2/1992 | Cragg |
| 5,098,405 A | 3/1992 | Peterson |
| 5,125,893 A | 6/1992 | Dryden |
| 5,143,853 A | 9/1992 | Walt |
| 5,147,332 A | 9/1992 | Moorehead |
| 5,149,327 A | 9/1992 | Oshiyama |
| 5,167,638 A | 12/1992 | Felix |
| 5,169,393 A | 12/1992 | Moorehead |
| 5,176,652 A | 1/1993 | Littrell |
| 5,176,662 A | 1/1993 | Bartholomew |
| 5,201,722 A | 4/1993 | Moorehead |
| 5,201,772 A | 4/1993 | Maxwell |
| 5,205,834 A | 4/1993 | Moorehead |
| 5,215,538 A | 6/1993 | Larkin |
| 5,249,598 A | 10/1993 | Schmidt |
| 5,253,765 A | 10/1993 | Moorehead |
| 5,254,086 A | 10/1993 | Palmer |
| 5,255,676 A | 10/1993 | Russo |
| 5,324,274 A | 6/1994 | Martin |
| 5,330,424 A | 7/1994 | Palmer |
| 5,336,203 A | 8/1994 | Goldhardt |
| 5,360,407 A | 11/1994 | Leonard |
| 5,370,624 A | 12/1994 | Edwards |
| 5,395,352 A | 3/1995 | Penny |
| 5,396,925 A | 3/1995 | Poli |
| 5,399,168 A | 3/1995 | Wadsworth, Jr. |
| 5,401,255 A | 3/1995 | Sutherland |
| D357,735 S | 4/1995 | Mcphee |
| 5,405,340 A | 4/1995 | Fageol |
| 5,411,491 A | 5/1995 | Goldhardt |
| 5,453,097 A | 9/1995 | Paradis |
| 5,454,784 A | 10/1995 | Atkinson |
| 5,469,805 A | 11/1995 | Gibbs |
| 5,470,305 A | 11/1995 | Arnett |
| 5,484,420 A | 1/1996 | Russo |
| 5,542,923 A | 8/1996 | Ensminger |
| 5,545,150 A | 8/1996 | Danks |
| 5,554,136 A | 9/1996 | Luther |
| 5,562,618 A | 10/1996 | Cai |
| 5,571,093 A | 11/1996 | Cruz |
| 5,575,769 A | 11/1996 | Vaillancourt |
| 5,619,393 A | 4/1997 | Summerfelt |
| 5,624,395 A | 4/1997 | Mikhail |
| 5,637,099 A | 6/1997 | Durdin |
| 5,667,500 A | 9/1997 | Palmer |
| 5,707,357 A | 1/1998 | Mikhail |
| 5,743,873 A | 4/1998 | Cai |
| 5,743,884 A | 4/1998 | Hasson |
| 5,743,894 A | 4/1998 | Swisher |
| 5,752,928 A | 5/1998 | de Roulhac |
| 5,752,938 A | 5/1998 | Flatland |
| 5,769,107 A | 6/1998 | Woodruff |
| 5,803,078 A | 9/1998 | Brauner |
| 5,807,349 A | 9/1998 | Person |
| 5,810,789 A | 9/1998 | Powers |
| 5,843,044 A | 12/1998 | Moorehead |
| 5,853,397 A | 12/1998 | Shemesh |

(56) References Cited

U.S. PATENT DOCUMENTS

| | | |
|---|---|---|
| 5,858,003 A | 1/1999 | Atala |
| 5,865,308 A | 2/1999 | Qin |
| 5,868,703 A | 2/1999 | Bertolero |
| 5,944,698 A | 8/1999 | Fischer |
| 5,984,902 A | 11/1999 | Moorehead |
| 5,989,233 A | 11/1999 | Yoon |
| 6,033,393 A | 3/2000 | Balbierz |
| 6,045,734 A | 4/2000 | Luther |
| 6,050,934 A | 4/2000 | Mikhail |
| 6,056,717 A | 5/2000 | Finch |
| 6,062,244 A | 5/2000 | Arkans |
| 6,081,106 A | 6/2000 | Camerlo |
| 6,092,551 A | 7/2000 | Bennett |
| 6,099,505 A | 8/2000 | Ryan |
| 6,110,154 A | 8/2000 | Shimomura |
| 6,120,483 A | 9/2000 | Davey |
| 6,152,129 A | 11/2000 | Berthon-Jones |
| 6,152,909 A | 11/2000 | Bagaoisan |
| 6,167,886 B1 | 1/2001 | Engel |
| 6,171,287 B1 | 1/2001 | Lynn |
| 6,210,366 B1 | 4/2001 | Sanfilippo, II |
| 6,227,200 B1 | 5/2001 | Crump |
| 6,270,489 B1 | 8/2001 | Wise |
| 6,296,316 B1 | 10/2001 | Hann |
| 6,306,124 B1 | 10/2001 | Jones |
| 6,322,541 B2 | 11/2001 | West |
| 6,364,861 B1 | 4/2002 | Feith |
| 6,364,867 B2 | 4/2002 | Wise |
| 6,375,637 B1 | 4/2002 | Campbell |
| 6,415,793 B1 | 7/2002 | Kretz |
| 6,436,077 B1 | 8/2002 | Davey |
| 6,442,415 B1 | 8/2002 | Bis |
| 6,446,671 B2 | 9/2002 | Armenia |
| 6,508,791 B1 | 1/2003 | Guerrero |
| 6,551,270 B1 | 4/2003 | Bimbo |
| 6,610,031 B1 | 8/2003 | Chin |
| 6,726,063 B2 | 4/2004 | Stull |
| 6,786,884 B1 | 9/2004 | Decant, Jr. |
| 6,874,999 B2 | 4/2005 | Dai |
| 6,929,631 B1 | 8/2005 | Brugger |
| 6,953,450 B2 | 10/2005 | Baldwin |
| 6,994,314 B2 | 2/2006 | Garnier |
| 7,025,744 B2 | 4/2006 | Utterberg |
| 7,081,106 B1 | 7/2006 | Guo |
| 7,252,652 B2 | 8/2007 | Moorehead |
| 7,291,133 B1 | 11/2007 | Kindler |
| 7,316,655 B2 | 1/2008 | Garibotto |
| 7,435,236 B2 | 10/2008 | Weaver |
| D595,846 S | 7/2009 | Racz |
| D596,288 S | 7/2009 | Racz |
| 7,601,141 B2 | 10/2009 | Dikeman |
| 7,637,893 B2 | 12/2009 | Christensen |
| 7,713,250 B2 | 5/2010 | Harding |
| 7,731,700 B1 | 6/2010 | Schytte |
| 7,758,541 B2 | 7/2010 | Wallace |
| 7,931,619 B2 | 4/2011 | Diamond |
| 7,947,032 B2 | 5/2011 | Harding |
| 7,951,121 B2 | 5/2011 | Weaver |
| 7,988,679 B2 | 8/2011 | Daly |
| 7,993,327 B2 | 8/2011 | Casey, II |
| D644,731 S | 9/2011 | Fangrow, Jr. |
| 3,034,035 A1 | 10/2011 | Karla |
| 8,079,987 B2 | 12/2011 | Moorehead |
| 8,083,721 B2 | 12/2011 | Miller |
| 8,105,314 B2 | 1/2012 | Fangrow, Jr. |
| 8,187,234 B2 | 5/2012 | Weaver |
| 8,257,321 B2 | 9/2012 | Lareau |
| 8,291,936 B2 | 10/2012 | Carmody |
| 8,328,768 B2 | 12/2012 | Quigley |
| 8,337,470 B2 | 12/2012 | Prasad |
| 8,343,113 B2 | 1/2013 | Hokanson |
| 8,377,011 B2 | 2/2013 | Weaver |
| 8,398,607 B2 | 3/2013 | Fangrow, Jr. |
| 8,444,628 B2 | 5/2013 | Fangrow, Jr. |
| 8,454,574 B2 | 6/2013 | Weaver |
| 8,454,579 B2 | 6/2013 | Fangrow, Jr. |
| 8,523,821 B2 | 9/2013 | Miller |
| 8,529,523 B2 | 9/2013 | Weaver |
| 8,540,685 B2 | 9/2013 | Moorehead |
| 8,585,660 B2 | 11/2013 | Murphy |
| 8,603,070 B1 | 12/2013 | Lareau |
| 8,628,515 B2 | 1/2014 | Fangrow, Jr. |
| 8,679,074 B2 | 3/2014 | Daly |
| 8,726,931 B2 | 5/2014 | Buiser |
| 8,753,320 B2 | 6/2014 | Miller |
| 8,758,306 B2 | 6/2014 | Lopez |
| 8,784,402 B1 | 7/2014 | Lareau |
| 8,789,558 B2 | 7/2014 | Volker |
| 8,870,850 B2 | 10/2014 | Fangrow, Jr. |
| 8,876,797 B2 | 11/2014 | Lareau |
| 8,926,571 B1 | 1/2015 | Keith |
| D722,155 S | 2/2015 | Wiegel |
| D722,156 S | 2/2015 | Wiegel |
| D722,157 S | 2/2015 | Wiegel |
| 9,044,541 B2 | 6/2015 | Blanchard |
| 9,186,494 B2 | 11/2015 | Fangrow |
| 9,192,753 B2 | 11/2015 | Lopez |
| 9,192,755 B2 | 11/2015 | Ravenscroft |
| 9,205,243 B2 | 12/2015 | Lopez |
| 9,206,283 B1 | 12/2015 | Santerre |
| 9,238,129 B2 | 1/2016 | Fangrow, Jr. |
| D752,215 S | 3/2016 | Blennnow |
| 9,278,206 B2 | 3/2016 | Fangrow |
| D757,259 S | 5/2016 | Duck |
| 9,447,892 B2 | 9/2016 | Lareau |
| 2001/0023333 A1 | 9/2001 | Wise |
| 2001/0037079 A1 | 11/2001 | Burbank |
| 2002/0010425 A1 | 1/2002 | Guo |
| 2002/0016584 A1 | 2/2002 | Wise |
| 2002/0026145 A1 | 2/2002 | Bagaoisan |
| 2002/0111662 A1 | 8/2002 | Iaizzo |
| 2002/0121530 A1 | 9/2002 | Socier |
| 2002/0156430 A1 | 10/2002 | Haarala |
| 2002/0157664 A1 | 10/2002 | Fugelsang |
| 2002/0165492 A1 | 11/2002 | Davey |
| 2002/0193752 A1 | 12/2002 | Lynn |
| 2003/0014015 A1 | 1/2003 | Tansey |
| 2003/0122095 A1 | 7/2003 | Wilson |
| 2003/0189067 A1 | 10/2003 | Stull |
| 2003/0195478 A1 | 10/2003 | Russo |
| 2004/0034324 A1 | 2/2004 | Seese |
| 2004/0064128 A1 | 4/2004 | Raijman |
| 2004/0102738 A1 | 5/2004 | Dikeman |
| 2004/0108479 A1 | 6/2004 | Garnier |
| 2004/0186444 A1 | 9/2004 | Daly |
| 2004/0193119 A1 | 9/2004 | Canaud |
| 2004/0210194 A1 | 10/2004 | Bonnette |
| 2004/0267185 A1 | 12/2004 | Weaver |
| 2005/0010176 A1 | 1/2005 | Dikeman |
| 2005/0027261 A1 | 2/2005 | Weaver |
| 2005/0043703 A1 | 2/2005 | Nordgren |
| 2005/0049555 A1 | 3/2005 | Moorehead |
| 2005/0149116 A1 | 7/2005 | Edwards |
| 2005/0165364 A1 | 7/2005 | DiMatteo |
| 2005/0171488 A1 | 8/2005 | Weaver |
| 2005/0171490 A1 | 8/2005 | Weaver |
| 2005/0171510 A1 | 8/2005 | DiCarlo |
| 2005/0283122 A1 | 12/2005 | Nordgren |
| 2006/0129092 A1 | 6/2006 | Hanlon |
| 2006/0135949 A1 | 6/2006 | Rome |
| 2006/0149189 A1 | 7/2006 | Diamond |
| 2006/0149211 A1 | 7/2006 | Simpson |
| 2006/0149214 A1 | 7/2006 | Breiter |
| 2007/0161940 A1 | 7/2007 | Blanchard |
| 2007/0161970 A1 | 7/2007 | Spohn |
| 2007/0163664 A1 | 7/2007 | Mijers |
| 2007/0276313 A1 | 11/2007 | Moorehead |
| 2008/0097341 A1 | 4/2008 | Casey |
| 2008/0108956 A1 | 5/2008 | Lynn |
| 2008/0200837 A1 | 8/2008 | Frazier |
| 2009/0177187 A1 | 7/2009 | Weaver Quigley |
| 2009/0292252 A1 | 11/2009 | Lareau |
| 2011/0062703 A1 | 3/2011 | Lopez |
| 2011/0087093 A1 | 4/2011 | Buiser |

(56) References Cited

U.S. PATENT DOCUMENTS

| | | |
|---|---|---|
| 2011/0118612 A1 | 5/2011 | Miller |
| 2011/0264054 A1 | 10/2011 | Miller |
| 2011/0313367 A1 | 12/2011 | Daly |
| 2011/0313368 A1 | 12/2011 | Weaver |
| 2012/0271247 A1 | 10/2012 | Weaver |
| 2012/0325351 A1 | 12/2012 | Volker |
| 2013/0060200 A1 | 3/2013 | Dalton |
| 2013/0220462 A1 | 8/2013 | Lareau |
| 2013/0338608 A1 | 12/2013 | Moorehead |
| 2014/0081285 A1 | 3/2014 | Kucklick |
| 2014/0163516 A1 | 6/2014 | Lareau |
| 2015/0135554 A1 | 5/2015 | Smith |
| 2016/0008530 A1 | 1/2016 | Weaver |
| 2016/0121041 A1 | 5/2016 | Weaver |

FOREIGN PATENT DOCUMENTS

| | | |
|---|---|---|
| DE | 20208420 | 10/2002 |
| EP | 0128525 | 12/1984 |
| EP | 0128625 | 12/1984 |
| EP | 0198962 | 10/1986 |
| EP | 0337617 | 10/1989 |
| EP | 0366814 | 5/1990 |
| EP | 0474069 | 3/1992 |
| EP | 0864336 | 9/1998 |
| EP | 0882466 | 12/1998 |
| EP | 0930082 | 7/1999 |
| EP | 1016431 | 7/2000 |
| EP | 2720881 | 4/2014 |
| EP | 2755060 | 7/2014 |
| FR | 2508008 | 12/1982 |
| FR | 2718969 | 10/1995 |
| GB | 2102398 | 2/1983 |
| JP | S576863 | 1/1982 |
| JP | S59133877 | 8/1984 |
| JP | S6088562 | 5/1985 |
| JP | S63255057 | 10/1988 |
| JP | H0231967 | 2/1990 |
| JP | H02102659 | 4/1990 |
| JP | H0528351 | 2/1993 |
| JP | H0645671 | 2/1994 |
| JP | H06121499 | 4/1994 |
| JP | H0938198 | 2/1997 |
| JP | H10512946 | 12/1998 |
| JP | H11500941 | 1/1999 |
| JP | H1147272 | 2/1999 |
| JP | 2000279527 | 10/2000 |
| JP | 2000514671 | 11/2000 |
| JP | 2001104486 | 4/2001 |
| JP | 2002505927 | 2/2002 |
| JP | 2002516160 | 6/2002 |
| JP | 2003047272 | 2/2003 |
| JP | 2003518984 | 6/2003 |
| JP | 2006500076 | 1/2006 |
| JP | 2007500039 | 1/2007 |
| JP | 2009539562 | 11/2009 |
| WO | 9206732 | 4/1992 |
| WO | 9516480 | 6/1995 |
| WO | 9617190 | 6/1996 |
| WO | 9623158 | 8/1996 |
| WO | 9723255 | 7/1997 |
| WO | 9726931 | 7/1997 |
| WO | 09726931 | 7/1997 |
| WO | 9822178 | 5/1998 |
| WO | 9942166 | 8/1999 |
| WO | 0006230 | 2/2000 |
| WO | 0044419 | 8/2000 |
| WO | 03084832 | 10/2003 |
| WO | 2005023355 | 3/2005 |
| WO | 2007146586 | 12/2007 |
| WO | 2008051647 | 5/2008 |
| WO | 2009112838 | 9/2009 |
| WO | 2009143116 | 11/2009 |
| WO | 2011008689 | 1/2011 |
| WO | 2011062767 | 5/2011 |
| WO | 09723255 | 12/2011 |
| WO | 2014014602 | 1/2014 |
| WO | 2014153302 A1 | 9/2014 |

OTHER PUBLICATIONS

Aw et al., Incidence and Predictive Factors of Symptomatic Thrombosis Related to Peripherally Inserted Central Catheters in Chemotherapy Patients, (2012), pp. 323-326.

Biffi, et al., A Randomized, Prospective Trial of Central Venous Ports Connected to Standard Open-Ended or Groshong Catheters in Adult Oncology Patients, American Cancer Society, pp. 1204-1212, May 2001.

Burns, The Vanderbilt PICC Service: Program, Procedural, and Patient Outcomes Successes, (2005), pp. 1-10, vol. 10 No. 4.

Carlo et al., A prospective Randomized Trial Demonstrating Valved Implantable Ports Have Fewer Complications and Lower Overall Cost Than Nonvalved Implantable Ports, (Aug. 7, 2004), pp. 722-727.

Carlson, et al., Safety Considerations in the Power Injection of Contrast Media Via Central Venous Catheters During Computed Tomographic Examinations, Investigative Radiology vol. 27, 1992, pp. 337-340.

Chahoud et al., "Randomized comparison of coronary angiography using 4F catheters: 4F manual versus 'Acisted' power injection technique," Catheter Cardiovasc Interv., vol. 53, No. 2, pp. 221-224 (2001).

Corrected Notice of Allowability dated Oct. 27, 2020 for U.S. Appl. No. 16/164,229 (pp. 1-6).

Elastomer. (2003). In The Macmillan Encyclopedia. Basingstoke, Hampshire: Macmillan Publishers Ltd. Retrieved Feb. 23, 2009 from http://www.credoreference.com/entry/3298087/.

English Translation of Office Action dated Aug. 18, 2009 for Japanese Patent Application No. 2006-517107 (3 pages).

English Translation of Office Action dated Jan. 28, 2011 for Japanese Patent Application No. 2006-517107 (3 pages).

English Translation of Office Action dated Mar. 29, 2010 for Japanese Patent Application No. 2006-517107 (2 pages).

Examination Report dated Apr. 6, 2006 for European Patent Application No. 04751644.8 (5 pages).

Examination Report dated Aug. 12, 2010 for European Patent Application No. 05722427.1 (6 pages).

Examination Report dated Mar. 26, 2010 for European Patent Application No. 05722427.1 (5 pages).

Extended Search Report dated Sep. 21, 2011 for European Patent Application No. 11173038.8 (5 pages).

Herts et al., "Power injection of contrast media using central venous catheters: feasibility, safety, and efficacy," AJR Am. J. Roentgenol., vol. 176, No. 2, pp. 447-453 (2001) 8 pages.

Herts et al., "Power injection of intravenous contrast material through central venous catheters for CT: in vitro evaluation," Radiology, vol. 200, No. 3, pp. 731-735 (1996).

Hoffer et al., Peripherally Inserted Central Catheters with Distal versus Proximal Valves: Prospective Randomized Trial, Society of Interventional Radiology, pp. 1173-1177, vol. 12 No. 10, Oct. 2001.

Hoffer et al., Prospective Randomized Comparison of Valved Versus Nonvalved Peripherally Inserted Central Vein Catheters, pp. 1393-1398, May 1999.

International Search Report PCT-US-05-011244—ISR dated Jun. 6, 2005.

International Preliminary Report on Patentability dated Jan. 3, 2006 for International Application No. PCT/US2004/014344 (7 pages).

International Preliminary Report on Patentability dated Jul. 31, 2006 for International Application No. PCT/US2005/001244 (8 pages).

International Preliminary Report on Patentability dated Nov. 23, 2010 for International Application No. PCT/US2009/044468 (7 pages).

International Search Report 10800375_SESR dated Jul. 10, 2014.
International Search Report 10800375-7_ESC dated Jul. 17, 2017.
International Search Report 11158827-3_ESO dated May 19, 2011.
International Search Report 11158827—ESR dated May 11, 2011.

(56) References Cited

OTHER PUBLICATIONS

International Search Report and Written Opinion dated Dec. 23, 2009 for International Application No. PCT/US2009/044468 (10 pages).
International Search Report and Written Opinion dated Jun. 6, 2005 for International Application No. PCT/US2005/001244 (12 pages).
International Search Report and Written Opinion dated Nov. 5, 2004 for International Application No. PCT/US2004/014344 (9 pages).
International Search Report and Written Opinion dated Sep. 3, 2010 for International Application No. PCT/US2010/041698 (10 pages).
International Search Report PCT-US-05-000761 IPRP dated Jul. 31, 2006.
International Search Report PCT-US-05-000761 ISR dated Dec. 4, 2005.
International Search Report PCT-US-05-000761—WOSA dated Jul. 29, 2006.
International Search Report PCT-US-05-001244 IPRP dated Jul. 31, 2006.
International Search Report PCT-US-09-044468 IPRP dated Nov. 23, 2010.
International Search Report PCT-US-09-044468 ISR dated Dec. 23, 2009.
International Search Report PCT-US-09-044468—WOSA dated Nov. 25, 2010.
International Search Report PCT-US-10-041698 ISR dated Sep. 2009.
International Search Report PCT-US-10-041698—ISR dated Dec. 2010.
International Search Report PCT-US 10-041698 IPRP dated Jan. 17, 2012.
International Search Report PCT-US 10-041698—IPRP dated Nov. 17, 2012.
Johnston et al., The Effect of Peripherally Inserted Central Catheter (PICC) Valve Technology on Catheter Occlusion Rates—The 'ELeCTRiC' Study, (2012), pp. 421-425.
Kaste et al., "Safe use of power injectors with central and peripheral venous access devices for pediatrict CT," Pediatr. Radiol., vol. 26, No. 8, pp. 449-501 (1996).
McMahon, Evaluating New Technology to Improve Patient Outcomes, pp. 250-255, vol. 25, No. 4, Jul./Aug. 2002.
Moureau, Nancy L., Glenda L. Dennis, Elizabeth Ames, and Robyn Severe. "Electrocardiogram (EKG) Guided Peripherally Inserted Central Catheter Placement and Tip Position: Results of a Trial to Replace Radiological Confirmation." Journal of the Association for Vascular Access 15.1 (2010): 8-14. Web.
Notice of Allowance dated Nov. 30, 2022 for U.S. Appl. No. 15/240,430 (pp. 1-10).
Notice of Allowance dated Aug. 21, 2020 for U.S. Appl. No. 16/229,469 (pp. 1-5).
Notice of Allowance dated Jun. 17, 2020 for U.S. Appl. No. 16/229,469 (pp. 1-5).
Notice of Allowance dated Sep. 10, 2020 for U.S. Appl. No. 16/164,229 (pp. 1-9).
Notice of Allowance dated Feb. 14, 2011 for European Patent Application No. 05722427.1 (6 pages).
Office Action dated Nov. 16, 2021 for U.S. Appl. No. 15/240,430 (pp. 1-17).
Office Action dated Jun. 7, 2011 for Canadian Patent Application No. 2,553,335 (4 pages).
Ong et al., Prospective Randomized Comparative Evaluation of Proximal Valve Polyurethane and Distal Valve Silicone Peripherally Inserted Central Catheters, (Aug. 2010), 1191-1196.
Pittiruti et al., A Prospective, Randomized Comparison of Three Different Types of Valved and Non-Valved Peripherally Inserted Central Catheters, pp. 519-523, no date given.
Poli et al., A Comparative Study on the Mechanical Behavior of Polyurethane PICCs, pp. 175-181, no date given.
Ricchezza et al., A Strategy for Reducing Catheter Occlusions and Infections: The Experience at St. Joseph's Hospital, (2009).
Rivitz et al., "Power injection of peripherally inserted central catheters," J. Vase. Interv. Radiol., vol. 8, No. 5, pp. 357-863 (1997).
Rogalla et al., Safe and easy power injection of contrast material through a central line, Eur. Radiol., vol. 8, No. 1, pp. 148-149 (1998).
Roth et al., "Influence of radiographic contrast media viscosity to flow through coronary angiographic catheters," Cathet. Cardiovasc. Diagn., vol. 22, No. 4, pp. 290-294 (1991) 5 pages.
Saito et al., "Diagnostic brachial coronary arteriography using a power-assisted injector and 4 French catheters with new shamps," J. Invasive Cardiol., vol. 9, No. 7pp. 461-468 (1997).
Walsh et al., "Effect of contrast agent viscosity and injection flow velocity on bolus injection pressures for peripheral Venous injection in first-pass myocardial perfusion studies," Technol. Health Care, vol. 10, No. 1, pp. 57-63 (2002).
Williamson et al., "Assessing the adequacy of peripherally inserted central catheters for power injection of intravenous contrast agents for CT," J Comput. Assist. Tomogr., vol. 25, No. 6, pp. 932-937 (2001).

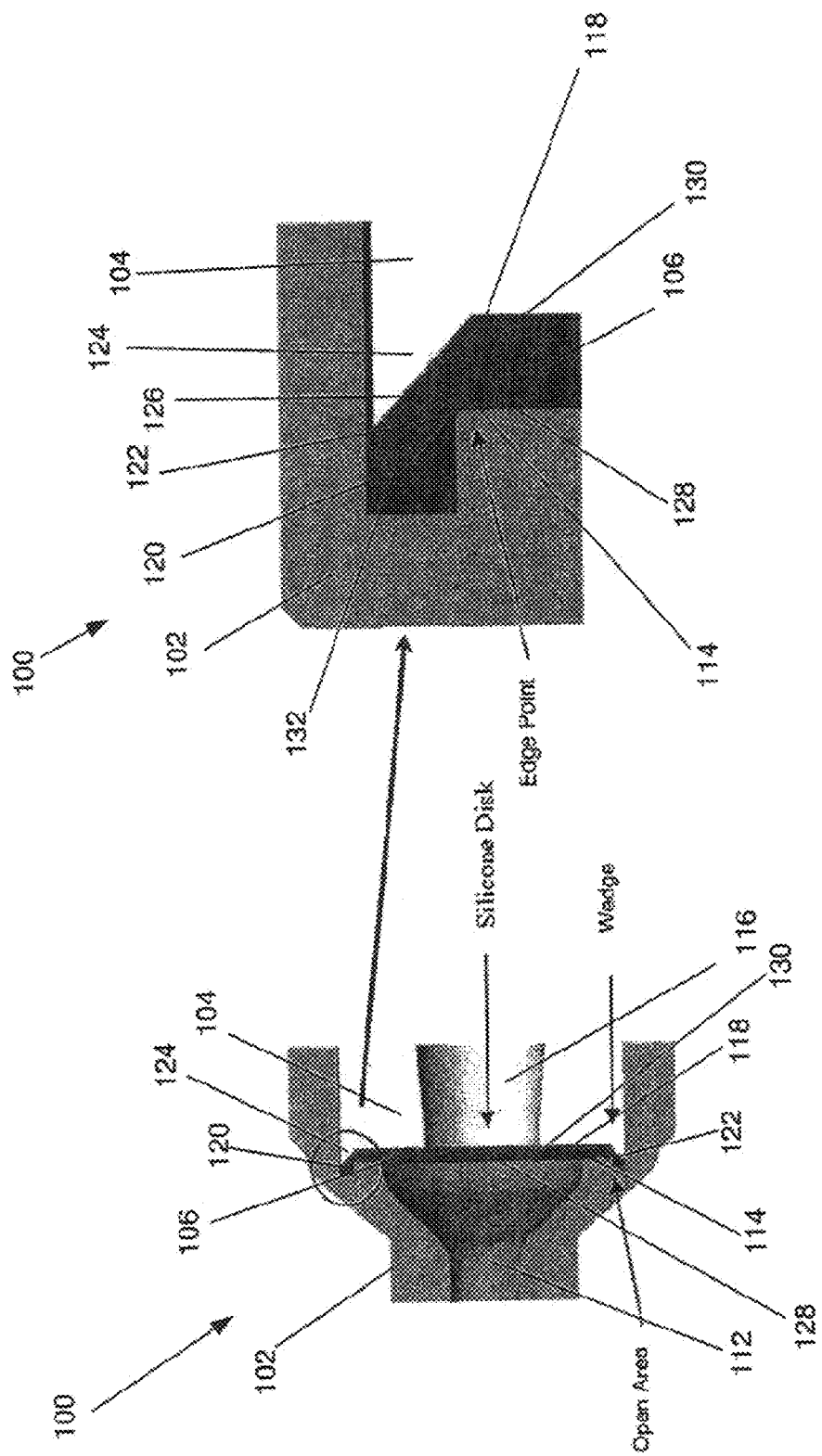

METHOD TO SECURE AN ELASTIC COMPONENT IN A VALVE

CROSS-REFERENCE TO RELATED APPLICATIONS

This application is a continuation of U.S. patent application Ser. No. 16/229,469, filed Dec. 21, 2018 (now U.S. Pat. No. 10,874,845), which is a continuation of U.S. patent application Ser. No. 14/272,918, filed May 8, 2014 (now U.S. Pat. No. 10,159,830), which is a continuation of U.S. patent application Ser. No. 13/176,054, filed Jul. 5, 2011 (now U.S. Pat. No. 8,753,320), which is a continuation of U.S. patent application Ser. No. 12/501,809, filed Jul. 13, 2009 (now U.S. Pat. No. 8,007,468), the disclosures of each of which are hereby incorporated by reference in their entirety.

BACKGROUND

Pressure activated safety valves have been incorporated into medical devices such as peripherally inserted central catheters (PICCs), ports, dialysis catheters and tunneled central catheters which provide long term access to the vascular system, etc. These valves generally include an elastic component that controls flow and/or pressure through the device to prevent flow therethrough when the device is not in use. The elastic component may be a slitted, flexible membrane extending across a lumen generally constructed so that, when subjected to a fluid pressure of at least a threshold magnitude, edges of the slit separate from one another to permit flow through the lumen. When the pressure applied to the membrane drops below the threshold level, the slit reseals to prevent leakage from or into the device. It is desirable to keep the flexible disk in place during high pressure and/or flow while maintaining the desired flow control characteristics of the membrane.

SUMMARY OF THE INVENTION

The present invention is directed to a valve comprising a flexible member including a slit formed on a central portion thereof and a first housing defining a first lumen extending therethrough, the first housing including a first contacting surface adapted, when the slit of the flexible member is aligned with the first lumen, to contact a first side of the flexible member the first housing defining a relief area extending about a perimeter of the first contacting surface radially outside the central portion relative to a longitudinal axis of the first lumen in combination with a second housing adapted to mate with the first housing with a second lumen defined by the second housing aligned with the first lumen and separated therefrom by the flexible member, the second housing including a second contacting surface which, when the first and second housings are mated to one another in an operative configuration with the flexible member pinched therebetween, contacts a second side of the flexible member opposite the first side thereof along the longitudinal axis, a radially outer portion of the second contacting surface including a protrusion aligning with and extending into the relief area when the first and second housings are mated in the operative configuration, the protrusion bending a peripheral portion of the flexible member about a radially outer edge of the first contacting surface into the relief area to maintain the flexible member at a desired position separating the first and second lumens so that, when subject to a fluid pressure of at least a predetermined magnitude, the slit of the flexible member opens to permit fluid transfer between the first and second lumens and, when subject to a fluid pressure less than the predetermined magnitude, the slit of the flexible member remains closed preventing fluid transfer between the first and second lumens.

BRIEF DESCRIPTION OF THE DRAWINGS

FIG. 2 shows a longitudinal cross-sectional view of a disk portion of the device of FIG. 1; and FIG. 3 shows an enlarged view of portion of an edge of the disk portion of the device shown in FIG. 2.

DETAILED DESCRIPTION

Figure 1:
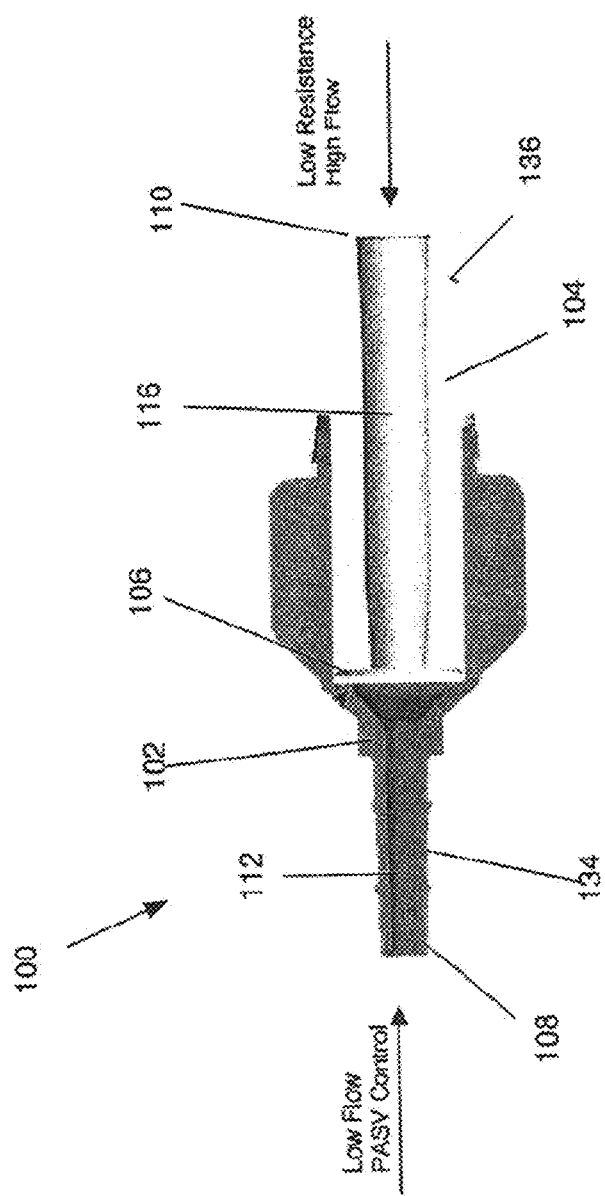
FIG. 1 shows a longitudinal cross-sectional view of a device according to an exemplary embodiment of the present invention.

The present invention may be further understood with reference to the following description and the appended drawings, wherein like elements are referred to with the same reference numerals. The present invention relates to an apparatus for controlling fluid flow through medical devices specifically for sealing devices which remain in place in the body to provide long term access to the vascular system. To improve the performance of pressure activated safety valves, exemplary embodiments of the present invention describe a wedge or other similarly shaped geometrical feature for fixing an elastic component and controlling an internal stress of the elastic component.

As shown in FIGS. 1-3, a device 100 according to an exemplary embodiment of the present invention comprises a first housing 102, a second housing 104 and an elastic component 106. As shown in FIG. 1, the first housing 102 and the second housing 104 may be coupled to one another to fix the elastic component 106 therebetween. For clarity, the elastic component 106 is shown between the first and the second housings 102, 104 before being pinched into the final position. The first housing 102 may form a distal end 108 of the device 100 and includes a first connection 134 for connecting to a first conduit which extends, for example, to a target body structure to and/or from which it is desired to transfer fluids. The second housing 104, at a proximal end 110 of the device 100, includes a second connection 136 for connecting to a second conduit which remains external to the body. The elastic component 106 is fixed between the first and the second housings 102, 104 to control a fluid flow therethrough.

The elastic component 106 may be any flexible membrane (e.g., in the form of a disk) including a slit (not shown) for controlling fluid flow therethrough such as, for example, a silicone disk. The elastic component 106 may operate as a bi-directional valve allowing fluid to flow through the device 100 in either direction whenever the valve is subjected to a fluid pressure of at least a threshold value. Alternatively, the elastic component 106 may operate as a uni-directional valve allowing fluid to flow in only one direction or having different threshold values for each of the two directions of flow therethrough. The elastic component 106 is configured to open only when fluid pressure exerted thereagainst reaches a predetermined threshold magnitude. The slit opens via a deformation of the elastic component 106 with edges of the slit moving away from one another to allow fluid to flow therethrough. Once fluid pressure falls below the threshold magnitude, the slit reseals preventing fluid from flowing therethrough. It will be understood by those of skill in the art that the elastic component 106 may include more than one slit extending therethrough.

As shown in FIGS. 2-3, the first housing 102 includes a lumen 112 extending therethrough and a disk-facing surface 114, which contacts the elastic component 106. The disk-facing surface 114 includes a substantially planar central portion 128 surrounding the lumen 112 and a relief area 120 radially outside the planar central portion 128 (relative to a longitudinal axis of tire first and second housings 102, 104). The relief area 120 may be formed as a recess extending around a radially outer edge of the disk-facing surface 114 for accommodating an outer perimeter 132 of the elastic component 106. The relief area 120 further includes an edge 122 over which the outer perimeter 132 of the elastic component 106 may be bent. It will be understood by those of skill in the art that the relief area 120 may be formed as either a continuous recess about the perimeter of the disk-facing surface 114 or as a series of recesses spaced from one another around the circumference of the disk-facing surface 114. In a preferred embodiment, the relief area 120 forms a ring-shaped recess about a circumference of the disk-facing surface 114.

The second housing 104 includes a lumen 116 extending therethrough and a disk-facing surface 118, which contacts the elastic component 106. The disk-facing surface 118 includes a substantially planar central portion 130 surrounding the lumen 116 and a protrusion 124 surrounding the planar central portion 130. The protrusion 124 extends distally away from the planar central portion 130 around a radially outer edge of the disk-facing surface 118. The protrusion 124 may be, for example, wedge-shaped including an angled surface 126 which contacts a radially outer portion of the elastic component 106 bending it over the edge 122 distally into the relief area 120. It will be understood by those of skill in the an that the protrusion 124 may extend continuously about the outer perimeter of the disk-facing surface 118 or may be formed as a series of protrusions separated from one another circumferentially about the outer perimeter of the disk-facing surface 118 by a series of recesses or gaps. In a preferred embodiment, the protrusion 124 is substantially ring-shaped and extends continuously around a circumference of the disk-facing surface 118.

The relief area 120 and the protrusion 124 of the first and die second housings 102, 104, respectively, enhance retention of the elastic component 106 applying compression to the elastic component 106 radially inward toward the longitudinal axis of the first and second housings 102, 104, respectively, to counteract tension to which the elastic component 106 is subjected as it is pinched between the first and second housings 102, 104 and stretched into the relief area 120. Initially, as the elastic component 106 is being pinched between the first and second housings 102, 104, as the outer edge of the elastic component 106 is bent around the edge 122 into the relief area 120, the central portion of the elastic component 106 is stretched radially outward drawing edges of the slit away from one another and puckering the central portion of the elastic component. Then, as the first and second housings 102, 104 are moved further toward one another, the elastic component 106 is pinched between the protrusion 124 and the edge 122 reducing a thickness of this portion of the elastic component 106 and urging the material pinched away from this area toward the slit—i.e., compressing the elastic component 106 radially to bring the edges of the slit back together sealing the valve. The planar portion 130 of the disk-facing surface 118 keeps the central portion of the clastic component 106 substantially flat so that the elastic component 106 does not pucker, aligning edges of the slit while under compression. In addition, the bending of the peripherally outer portion of the elastic component 106 over the edge 122 into the relief area 120 reduces the likelihood that the elastic component 106 will be pulled out of position between the first and second housings 102, 104 when subjected to excess pressure. That is, the outer perimeter 132 of the clastic component 106 extends radially outward of the edge 122 in the relief area 120 with the outer perimeter 132 acting as an anchor holding the elastic component 106 in place.

It will be understood by those of skill in the art that the compression force for closing the slit may be controlled by altering the angle of the angled surface 126 and a position of the protrusion 124 in relation to the edge 122. In a preferred embodiment, the angled surface 126 may be angled from between approximately 40E to 50E and more preferably, at an angle of approximately 45E. The location of the edge 122 may be determined by the angled surface 126, which is positioned to the periphery of the flexible member 106. Thus, the compression force may be controlled as desired. It will also be understood by those of skill in the art that the amount of compression on the slit and/or the elastic component 106 is one of the factors determining the pressure gradients needed to open and close the slit. Other factors may include, for example, a flexibility, a thickness, and a material of the elastic component 106.

It will be apparent to those skilled in the art that various modifications and variations may be made in the structure and the methodology of the present invention, without departing from the spirit or scope of the invention. Thus, it is intended that the present invention cover the modifications and variations of this invention provided that they come within the scope of the appended claims and their equivalents.

The invention claimed is:

1. A device comprising:
   a disk member comprising a slit;
   a first housing defining a first lumen extending therethrough, the first housing comprising a first contacting surface adapted to contact a first side of the disk member, the first housing defining a relief area extending around a perimeter of the first contacting surface; and
   a second housing defining a second lumen extending therethrough, and the second housing comprising a second contacting surface that contacts a second side of the disk member, a radially outer portion of the second contacting surface comprising a protrusion that aligns with the relief area when the first and second housings are in contact, the protrusion contacting the disk member such that a peripheral portion of the disk member extends into the relief area, and wherein the protrusion extends substantially and continuously around a perimeter of the second contacting surface.

2. The device of claim 1, wherein the disk member is configured to move at a predetermined fluid pressure.

3. The device of claim 1, wherein the protrusion is substantially wedge-shaped.

4. The device of claim 1, wherein the protrusion extends into the relief area.

5. The device of claim 1, wherein a portion of the contacting surface radially within the protrusion is substantially planar and extends annularly about the second lumen.

6. The device of claim 1, wherein the disk member is a bi-directional valve.

7. The device of claim 1, wherein the disk member is a uni-directional valve.

8. The device of claim 2, wherein the predetermined pressure is selected to be above the pressures to which the disk member will be subjected due to natural fluctuations in a fluid pressure within a target body structure.

9. The device of claim 1, wherein the disk member has a first predetermined pressure for flow therethrough from a proximal side to a distal side thereof and a second predetermined pressure different from the first predetermined pressure for flow therethrough from a distal side to a proximal side thereof.

10. A device comprising:
a flexible valve member comprising at least two slits;
a first housing defining a first lumen extending therethrough, the first housing including a first contacting surface adapted to contact a first side of the flexible valve member, the first housing defining a relief area extending about a perimeter of the first contacting surface; and
a second housing defining a second lumen, the second housing including a second contacting surface that contacts a second side of the flexible valve member, a radially outer portion of the second contacting surface including a protrusion that aligns with the relief area when the first and second housings are mated together, the protrusion contacting the flexible valve member such that a peripheral portion of the flexible valve member extends into the relief area, and wherein the protrusion extends substantially and continuously around a perimeter of the second contacting surface.

11. The device of claim 10, wherein the flexible valve member is in the form of a disk.

12. The device of claim 10, wherein the flexible valve member is configured to flex when a predetermined fluid pressure is achieved, thereby opening at least one of the two slits.

13. The device of claim 12, wherein the movement of the flexible member results in deformation of the flexible valve member such that a first edge and a second edge of at least one of the two slits move away from one another.

14. The device of claim 10, wherein a compression force for closing one of the at least two slits is a result of the position of the protrusion relative to an edge of the second housing.

15. A device comprising:
a bi-directional valve comprising an elastic member, and a slit;
a first housing defining a first lumen extending therethrough, the first housing including a first contacting surface adapted to contact a first side of the elastic member, the first housing defining a relief area extending about a perimeter of the first contacting surface; and
a second housing configured to mate with the first housing, the second housing defining a second lumen and is separated from the first housing by the elastic member, the second housing including a second contacting surface that contacts a second side of the elastic member, a radially outer portion of the second contacting surface including a protrusion that aligns with the relief area when the first and second housings are mated, the protrusion contacting the elastic member such that a peripheral portion of the elastic member extends into the relief area, and wherein the protrusion extends substantially and continuously around a perimeter of the second contacting surface.

16. The device of claim 15, wherein the bi-directional valve is configured to allow fluid to flow through the device in either direction whenever the bi-directional valve is subjected to a predetermined fluid pressure.

17. The device of claim 15, wherein the first and second housings are mated to one another in an operative configuration with the elastic member located there between.

18. The device of claim 15, wherein the protrusion extends into the relief area.

19. The device of claim 15, wherein the protrusion includes an angled surface.

20. The device of claim 15, wherein the protrusion is substantially ring-shaped.

\* \* \* \* \*